United States Patent [19]
Chien et al.

[11] Patent Number: 4,883,669
[45] Date of Patent: Nov. 28, 1989

[54] TRANSDERMAL ABSORPTION DOSAGE UNIT FOR ESTRADIOL AND OTHER ESTROGENIC STEROIDS AND PROCESS FOR ADMINISTRATION

[75] Inventors: Yie W. Chien, North Brunswick; Chia-Shun Lee, Highland Park, both of N.J.; Kirti H. Valia, Indianapolis, Ind.; Te-Yen Chien, Piscataway, N.J.

[73] Assignee: Rutgers, The State University of New Jersey, New Brunswick, N.J.

[21] Appl. No.: 868,709

[22] Filed: May 30, 1986

Related U.S. Application Data

[63] Continuation-in-part of Ser. No. 705,194, Feb. 25, 1985, and a continuation-in-part of Ser. No. 770,968, Aug. 30, 1985, abandoned.

[51] Int. Cl.$^4$ .............................................. A61F 13/02
[52] U.S. Cl. .................................... 424/448; 424/449; 424/486
[58] Field of Search ................ 424/449, 448; 514/946, 514/947

[56] References Cited

U.S. PATENT DOCUMENTS

| | | | |
|---|---|---|---|
| 3,996,934 | 12/1976 | Zaffaroni | 424/449 |
| 4,053,580 | 10/1977 | Chien et al. | 424/449 |
| 4,291,014 | 9/1981 | Kieth et al. | 424/486 |
| 4,300,820 | 11/1981 | Shah | 424/80 X |
| 4,336,243 | 6/1982 | Sanvordeker et al. | 424/449 |
| 4,460,372 | 8/1984 | Campbell et al. | 424/449 |
| 4,693,887 | 9/1987 | Shah | 424/80 X |

*Primary Examiner*—Thurman K. Page
*Assistant Examiner*—Leon R. Horne
*Attorney, Agent, or Firm*—Leroy G. Sinn

[57] ABSTRACT

This invention relates to a novel transdermal absorption dosage unit comprising a backing layer, an adjoining layer of solid polymer matrix in which estradiol or another steroidal pharmaceutical having estrogenic activity is microdispersed; and a biologically acceptable adhesive means by which the dosage unit adheres to the skin of the subject being administered said estradiol or another said steroidal pharmaceutical and adapted to permit transdermal absorption of said estradiol or another said steroidal pharmaceutical. Additionally, the invention relates to improved estradiol or other estrogenic steroid maintenance therapy.

20 Claims, No Drawings

TRANSDERMAL ABSORPTION DOSAGE UNIT FOR ESTRADIOL AND OTHER ESTROGENIC STEROIDS AND PROCESS FOR ADMINISTRATION

CROSS-REFERENCE TO RELATED APPLICATIONS

This application is a continuation-in-part of both U.S. application Ser. No. 06/705,194, filed Feb. 25, 1985, by Yie W. Chien and Chia-Shun Lee and U.S. application Ser. No. 06/770,968, filed Aug. 30, 1985, by Yie W. Chien and Chia-Shun Lee now abandoned.

TECHNICAL FIELD

This invention relates to a novel transdermal absorption dosage unit comprising a backing layer, an adjoining layer of solid polymer matrix in which estradiol or another steroidal pharmaceutical having estrogenic activity is microdispersed; and a biologically acceptable adhesive means by which the dosage unit adheres to the skin of the subject being administered said estradiol or another said steroidal pharmaceutical and adapted to permit transdermal absorption of said estradiol or said another steroidal pharmaceutical. Additionally, the invention relates to improved estradiol or other estrogenic steroid maintenance therapy.

BACKGROUND ART

It has been found that certain pharmaceuticals are absorbed to a degree through the skin. This is referred to as transdermal pharmaceutical absorption. One means of effecting transdermal absorption has been to distribute the pharmaceutical within a polymeric disc or a container of a gel, which is brought into contact with an area of the skin of the subject to be treated with the pharmaceutical. Also, ointments or lotions containing a desired pharmaceutical have been applied to an area of the skin of the subject to be treated. Problems encountered in such treatment include inadequate control over the rate and duration of transdermal absorption or the rate can be too slow in the case of certain dosage forms, especially from pharmaceutical-containing discs or pharmaceutical-containing gel container dosage units or pads. It has been found that the transdermal absorption rates of certain pharmaceuticals can be increased by use of absorption promoting compounds (also referred to as skin permeation enhancers) with the pharmaceutical to be absorbed when compounding the polymeric disc or the pharmaceutical-containing gel.

It is desired to improve the dosage unit forms or devices by which pharmaceuticals are transdermally absorbed, especially in view of the importance of administration of pharmaceuticals by this means. Desired transdermal absorption of pharmaceuticals would provide an avoidance of gastrointestinal incompatibility with the pharmaceuticals and unwanted destruction of the pharmaceutical by metabolism in the gastrointestinal tract and by a "first pass" hepatic metabolism. The transdermal absorption minimizes inter- and intra-patient variations regarding such incompatibilities and metabolisms. By transdermal absorption, it is deemed possible to provide more constant pharmaceutical concentration in the body and to realize a greater pharmaceutical efficiency. It is possible, by proper transdermal absorption, to reduce the frequency of effective dosing. Transdermal administration provides most of the advantages of intravenous dosing without the necessity of hospitalization and the accompanying discomfort and inconvenience.

With regard to specific pharmaceuticals to which this invention is directed, the estrogenic steroid estradiol is an illustration of a pharmaceutical in which great loss of orally administered estrogen occurs by first-pass through the liver, it being almost completely metabolized. Therefore, oral administration of estradiol is not a satisfactory means of replacing normal levels of estradiol. It has been found that by transdermal administration, estradiol can be provided, in only a fraction of the amount required in oral dosing, to achieve adequate levels of estradiol, which the body for one or more reasons is not naturally producing to provide adequate levels in women to prevent body conditions and symptoms caused by such inadequate levels. Also, by transdermal administration of estradiol, for example, the unwanted estradiol metabolites produced by first-pass hepatic metabolism are greatly reduced. An additional advantage of transdermal administration is the attainment of more constant levels of estradiol and other estrogenic steroids.

The need for estradiol replacement therapy is caused by menopause (the cessation of ovarian function), oophorectomy (loss of one or both ovaries by surgery) or by pituitary failure. Replacement estrogenic therapy is an important need. Besides the need to alleviate the menopausal symptoms caused by estrogenic steroid deficiency, there are additional contributions of such replacement estrogenic therapy associated with osteoporosis (loss of bone mass) and atherosclerosis. There is clearly a need for improvements in means and methods for estrogenic steroid therapy. Even though it has been found that estradiol itself or estradiol in the form of certain derivatives such as mono- or diesters (e.g., acetate esters) can be absorbed transdermally, it is desired that improved transdermal estradiol and other estrogenic steroid absorption dosage unit forms and processes of transdermal administration be developed. A number of advantages would result.

SUMMARY OF INVENTION

This invention relates to an improved transdermal pharmaceutical-containing dosage unit comprising:
 (a) a backing layer which is substantially impervious to the pharmaceutical to be delivered transdermally;
 (b) a polymer matrix disc layer which is in contact with said backing layer and which has microdispersed therein an amount of estradiol or other estrogenic steroid capable of transdermal absorption or pharmacologically acceptable derivatives thereof which are capable of transdermal absorption, said disc layer providing a dosage amount of the pharmaceutical to be delivered transdermally; and
 (c) an adhesive means which adheres the dosage unit in intimate contact with the skin of the subject being treated to permit the pharmaceutical to be absorbed transdermally.

The backing layer is made from materials that are substantially impermeable with regard to the pharmaceutical of the transdermal dosage unit. It can be made of polymers such as polyethylene, polypropylene, polyvinylchloride, polyesters such as poly(ethylene phthalate), and foils such as laminates of polymer films with metallic foils such as aluminum foil.

The polymer matrix disc layer is suitably fabricated from biologically acceptable lipophilic polymers. The polymer matrix disc layer which has the pharmaceutical distributed therein can suitably be made of a medical-grade silicone polymer such as a polydimethylsiloxane polymer. The silicone polymer can also be a block or graft or other type copolymer. The pharmaceutical is suitably dispersed in the silicone polymer, to which mixture a curing agent is suitably added. The polymer-pharmaceutical mixture is then formed into a layer of an appropriate thickness and suitable surface area and is cured, if desired. The matrix layer is adhered to the backing layer. Other suitable polymers which can be used in the formulation of the polymer matrix disc layer are elastomers or thermoplastics. Care must be taken that the polymer selected is compatible with the pharmaceutical, permits its release for transdermal absorption and is free or sufficiently free from any biologically unacceptable components.

A suitable derivative of estradiol or other estrogenic steroid used in formulating the polymer matrix disc layer is commonly an ester which is biologically compatible and can be absorbed effectively transdermally. Also, it is ordinarily desired that such esters are bioconvertible by components of the skin or other portions of the body such as hydrolytical enzymes (e.g., esterase) to estradiol or other desired estrogenic steroid. If the derivative is an ester, the derivative can be a mono- or di-ester if the estrogenic steroid has two esterifiable groups. In the case of estradiol, it has hydroxy groups at the 3- and 17- positions and therefore the 3-mono and 17-mono as well as the 3,17 diesters can be made by generally known esterification methods. Some ester derivatives will be absorbed more readily than the basic estradiol or other estrogenic steroid, which is the basic compound. In selection of ester derivatives, it is ordinarily preferred that the ester derivative be absorbed more effectively than the basic compound and bioconverts efficiently, after absorption, to estradiol or other basic estrogenic steroid used. Valerate mono- and di-esters of estradiol are presently considered to be desirable esters. In formulating the polymer disc layer, it is desirable at times to utilize two or more pharmaceuticals, such as the combination of an estradiol ester, like estradiol valerate, with an amount of estradiol. Also, one estrogenic steroid either in the form of the basic compound or derivative such as a bioconvertible ester, or combinations thereof, can be combined with another steroid which has a different efficacy, such as a progestin, in a suitable amount in order to provide appropriate estrogenic therapy.

Finally, the adhesive means of the dosage unit is assembled with the other layer elements to form the dosage units. The adhesive means selected can vary depending on many factors including economic factors such as the type of manufacturing equipment most readily available, the rapidity of absorption desired or other factors. For example, the adhesive layer can be applied directly to the polymer matrix disc layer. A skin permeation enhancer compound can be mixed thoroughly with the adhesive polymer which is suitable for adhesion to the skin locus to which the transdermal matrix dosage unit will be applied. The adhesive polymer-skin permeation enhancer layer can be applied to the polymer matrix disc layer by spraying or by solvent casting or laminating. The concentration of skin permeation enhancer compound, if employed, can be reduced in the portion of the adhesive layer means, especially if less than desired adhesion is realized in the adhesive layer, by applying the surface portion of the adhesive layer separately wherein the adhesive composition has a lower concentration of skin permeation enhancer compound. The adhesive layer is desirably thin in the micron-range thickness, suitable 10–200 microns in thickness, desirably about 20 to 180 microns, and preferably about 30 to 150 microns in thickness. An effective amount of a skin permeation enhancer compound can also be incorporated into the pharmaceutical-containing disc layer. Also, if desired, the adhesive means can be in the form of a ring adhered to the backing layer which extends beyond the circumference of the disc layer. When such a concentric ring adhesive means is employed, the exposed surface of the pharmaceutical-containing disc layer is held in intimate contact with the skin of the subject treated.

The absorption rate of the transdermal pharmaceutical absorption dosage units of the invention can be increased, such as by having an Enhancing Factor of at least 1.2, preferably at least 1.3, and more preferably at least about 1.5. Enhancing Factor is defined as the ratio of normalized permeation rate [in $mcg/cm^2/hr$] of a dosage unit of this invention with skin permeation enhancer/the normalized permeation rate of a corresponding dosage unit without enhancer.

The invention also is a process for administering said pharmaceutical transdermally by forming pharmaceutical-containing polymer matrix disc dosage unit having a polymer matrix disc layer which has the pharmaceutical dosage dispersed therein, to which matrix disc is adhered a backing layer, said dosage unit having assembled therewith an adhesive mean to hold the dosage unit in intimate contact with the skin of the subject treated so that the pharmaceutical is absorbed transdermally, and by applying said dosage unit by way of said adhesive means to the skin of the subject to be treated, whereby said pharmaceutical is transdermally administered to said subject to achieve systemic effects.

DETAILED DESCRIPTION OF THE INVENTION AND THE PREFERRED EMBODIMENTS

The backing layer can be made of any suitable material which is impermeable to the pharmaceutical of the polymer matrix layer. The backing layer serves as a protective cover for the matrix layer and provides also a support function. The backing can be formed so that it is essentially the same size layer as the pharmaceutical-containing matrix disc layer or it can be of larger dimension so that it can extend beyond the side of the matrix disc layer or overlay the side or sides of the pharmaceutical-containing disc layer and then can extend outwardly in a manner that the surface of the extension of the backing layer can be the base for an adhesive means. The adhesive means holds the dosage unit in intimate contact with the skin of the subject treated. Examples of materials suitable for making the backing layer are films of high and low density polyethylene, polypropylene, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the polymer matrix layer. The backing layer can be any appropriate thickness which will provide the desired protective and support functions. A suitable thickness will be from about 10 to about 200 microns. Desirably, the thickness will be from about 20 to about 150 microns, and preferably be from about 30 to about 100 microns.

The polymer matrix layer can be made from silicone elastomers of the general polydimethylsiloxane structure, such as silicone polymers of the following general formula:

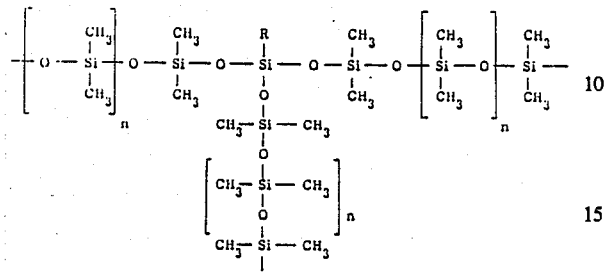

wherein R is alkyl or alkoxy containing 1-7 carbon atoms, vinyl or phenyl and wherein n is about 100 to about 5000.

The silicone polymers selected preferably are cross-linkable at moderate temperatures such as room temperature, using cross-linking catalysts which are biologically acceptable in the final polymer matrix and which are compatible with the pharmaceutical component to be used in making the polymer matrix dosage forms. Various suitable crosslinking agents can be used in crosslinking the above polymer such as tetrapropoxy silane [Si(OCH$_2$CH$_2$CH$_3$)$_4$] if the silicone polymer has free hydroxy groups such as terminal hydroxy groups. A tin catalyst can be used for such crosslinking reaction. If a silicone polymer component has vinyl groups, it can be crosslinked with a dimethyl-silicone polymer using a catalyst such as a platinum catalyst. Some suitable silicone polymers are cross-linkable copolymers having dimethyl and methylvinyl siloxane units, which can be cross-linked as by using a suitable peroxide catalyst. Other cross-linking sites can be present in the polysiloxane elastomers used. Suitable silicone medical-grade polymers are sold under the designations Silastic 382, Q7-4635, Q7-4650, Q7-4665, Q7-4735, Q7-4750, Q7-4765 and MDX-4-4210.

The silicone polymers selected can also have a "block" or "graft" structure or both. By "block" structure is meant that the polymer can have a section or block of the polymer chain structure of the polymer which can have a repeating unit of one type, such as dimethylsiloxane, and then have a succeeding block made up of repeating units of another type, such as methylvinylsiloxane, diphenylsiloxane, diisopropyl siloxane units or other siloxane or silane units or even of monomer units of a compatible non-siloxane or non-silane type. The blocks can vary in length and be repeated as desired. For example, if the blocks are represented as "A" and "B", respectively, the block copolymer can be A-B or A-B-A or A-B-A-B, etc. The "graft" structure simply means that to the main polymer chain, one or more polymer chains are attached. Those grafted chains can have the same polymer units as those of the main chain or can be different, as described above in connection with "block" copolymers. Also, the polymer used can be of a different type wherein copolymerizable monomers are placed together in a polymerization reactor so the main chain can have a certain population of each of the monomeric units.

The following are examples of block copolymers of the type which can be utilized in this invention.

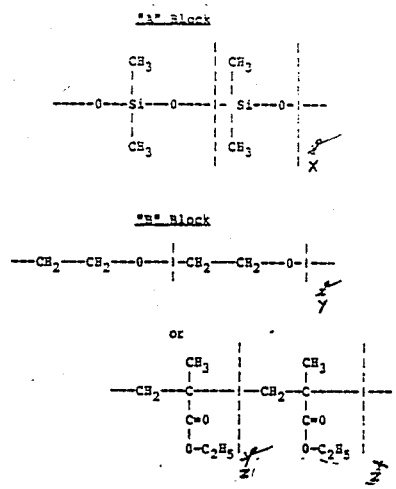

wherein x,y and z represent the number of repeating units sufficient to provide the desired property in the polymer, such as from about 10 to about 5000.

Generally, those polymers used to form the biologically acceptable polymer matrix are those capable of forming thin walls or coatings through which pharmaceuticals can pass at a controlled rate. Suitable polymers are biologically and pharmaceutically compatible, non-allergenic and insoluble in and compatible with body fluids or tissues with which the device is contacted. The use of soluble polymers is to be avoided since dissolution or erosion of the matrix would affect the release rate of the pharmaceutical as well as the capability of the dosage unit to remain in place for convenience of removal.

Exemplary materials for fabricating the biologically acceptable polymer matrix include polyethylene, polypropylene, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, chlorinated polyethylene, polyvinyl chloride, vinyl chloride-vinyl acetate copolymer, polymethacrylate polymer (hydrogel), polyvinylidene chloride, poly(ethylene terephthalate), butyl rubber, epichlorohydrin rubbers, ethylene-vinyl alcohol copolymer, ethylene-vinyloxyethanol copolymer; silicone copolymers, for example, polysiloxane-polycarbonate copolymers, polysiloxane-polyethyleneoxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxypropyl methyl cellulose, and cellulose esters; polycarbonates; polytetrafluoroethylene; and the like. For best results, the biologically acceptable polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after microdispersing the pharmaceutical into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

The adhesive means is suitably made in the form of a layer covering the pharmaceutical-containing disc and using a silicone adhesive, such as a polydimethylsiloxane adhesive depicted by the following formula:

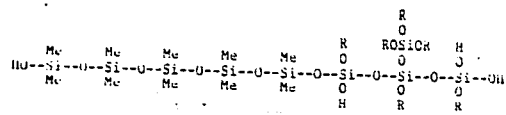

wherein Me is methyl and R is Si(CH3)3

For example, adhesive products or amine-resistant adhesive products sold by Dow Corning, such as the one sold under the designation DC-355, are suitable for use in making the adhesive layer. The adhesive polymer must be biologically acceptable and compatible with the pharmaceutical and skin permeation enhancer, if used. Certain polyacrylic adhesive polymers (in the form of an alkyl ester, amide, free acid, or the like) or polyisobutylene adhesive polymers can also be used with some pharmaceuticals. Other suitable hypoallergenic pressure-sensitive contact adhesive compositions can be used. A preferred adhesive layer is pressure-sensitive.

However, if desired depending upon economic and other factors, the adhesive means can be in the form of a ring attached, for example, to an extended portion of the backing layer so that the adhesive layer is adjacent to the sidewall of the pharmaceutical-containing disc layer. The width of such adjacent adhesive ring must be adequate to hold the dosage unit securely to the subject being treated. Ordinarily, a suitable width of such adhesive ring can be about 0.2 to about 1.2 cm, preferably about 0.3 to about 1.0 cm.

The adhesive means then is finally covered in conventional therapeutic practice with a releasable protective film layer which is made from materials which are substantially impermeable to the pharmaceutical, the skin permeation enhancer if used and any other components of the polymer matrix dosage unit. The polymer materials and metal foil laminates used for the backing layer can be used to make the protective layer, provided the layer is made strippable or releasable such as by applying conventional siliconizing. A suitable releasable material for use with silicone polymer adhesive DC-355 is Scotchpak 1022 material sold by the 3M Company.

In making the pharmaceutical-containing polymer matrix disc layer, silicone elastomers such as polydimethylsiloxane of the formula described above can suitably be used. In making estradiol-dispersed polymer matrix disc dosage units, it has been found suitable to use a polyol such as polyethylene glycol as a dispersing agent. Other suitable dispersing agents can be used instead so long as they are effective. Water-soluble polyols are generally suitable. For example, polyethylene glycols, such as those having a molecular weight of about 400, can be used, the molecular weight being variable therefrom, such as suitably between 300 and 500. Other suitable dispersing agents known to the formulating art can be used. Depending upon the steroidal pharmaceutical and the drug loading desired, a suitable amount of a dispersing agent can be varied from zero to about 50 percent (by weight) based on the weight of the polymer matrix disc. Commonly, the polyol is added as an aqueous solution with the polyol content varying from 10 to about 50 percent, based on the weight of the final polymer matrix. Aqueous solutions having about 40 percent polyol ordinarily are suitable, with some variation depending upon the rate of permeation desired, the particular steroidal pharmaceutical used, and at times, other factors. The pharmaceutical then is added to the polymer used to make the matrix disc layer. The amount of the pharmaceutical added depends upon the amount of pharmaceutical dosage desired in each dosage unit and the amount which can be incorporated into the polymer matrix disc to retain suitable structural, diffusion an other properties in the final matrix disc. It has been found, for example, that the pharmaceutical can be satisfactorily added to 70 parts of the polymer used in making the matrix disc, such as silicone elastomers. It has been found to be preferable to dissolve and disperse the steroidal pharmaceutical used in an amount of a selected aqueous solution of polyol, such as PEG 400. The mixture of the polymer and pharmaceutical or pharmaceutical-dispersing aqueous polyol solution is then thoroughly mixed using a high-torque mixer to form a homogeneous microdispersion of the pharmaceutical in the polymer. With continued agitation, an amount of cross-linking catalyst is desirably added together with a relatively low molecular weight polymer having a compatible chemical structure. For example, when polydimethylsiloxane based polymer is used as the polymer, a relatively low molecular weight polydimethylsiloxane and a cross-linking catalyst is added (such as 10 parts by weight of the low molecular weight polydimethylsiloxane and 30 drops of stannous octanoate per 100 g. amount of the final polydimethylsiloxane-pharmaceutical mixture) to the above illustrative composition of 20 parts of pharmaceutical dispersion and 70 parts of polydimethylsiloxane polymer. Again, the mixture is agitated with a high-torque mixer to form a uniform admixture. After each mixing step, the composition is subjected to vacuum to remove entrapped air.

The deaereated mixture is then placed in a device maker and heated to a suitable elevated temperature to promote cross-linking. A suitable temperature for cross-linking when the polymer used is polydimethylsiloxane of the above formula and the cross-linking catalyst is stannous octanoate, is from about 10° C. to about 200° C., desirably about 20° C. to about 100° C. The temperature used should not cause significant degradation of the pharmaceutical. The polymer matrix sheet desirably is about 0.05 to 5 mm, preferably about 0.1 to about 3 mm in thickness. The resulting cross-linked polymer matrix sheet 1s removed from the device maker and can be cut to form discs with desired shapes and sizes. The discs are then attached to a backing sheet, as described above, using an adhesive. The disc alternatively can be made directly on the backing sheet used. The discs generally should not exceed about 100 sq. cm in area, suitably about 5 to 100 sq. cm, preferably, about 8 to about 80 sq. cm, generally about 10 to 60 sq. cm being more preferable. The shape of the discs can vary; they can be circular, square, rectangular or other desired shape.

The pharmaceutical-containing polymer matrix disc layer, generally speaking, should contain some excess of the dispersed pharmaceutical over the dosage amount desired to be transdermally absorbed by the subject to be treated. Ordinarily, this excess is small, such as less than 2-fold excess. Generally speaking, an amount of the pharmaceutical used, which is sufficient, is less than 2 to about 10 times the desired dosage to about less than 2 to 5 times the desired dosage to be transdermally absorbed being adequate, depending upon the physiochemical properties of the pharmaceutical, as well as the nature of the polymer of the matrix disc layer and other factors.

The adhesive means if it contains a skin permeation enhancer is made as by dissolving the enhancer compound in a solvent for the enhancer which is compatible with the adhesive polymer solution used to make the adhesive layer containing the skin permeation enhancer. Any suitable amount of solvent can be used as necessary to dissolve the quantity of enhancer to be admixed with the adhesive polymer solution used. For example, 3 to 10 parts of solvent can be used to dissolve one part of skin permeation enhancer, depending upon the solubility of the enhancer. When using polydimethylsiloxane adhesive solution, it has been found suitable to use 2 to 20 parts of skin permeation enhancer in 20 to 50 parts of solvent (such as acetone, methyl ethyl ketone, trifluorotrichloroethane or other suitable solvent) and add the solution to 100 parts of the adhesive solution. The enhancer - adhesive combination is thoroughly mixed and a coating thereof is applied using a film coating machine, directly onto the polymer matrix or to a strippable release liner before laminating onto the polymer matrix, as described above. A suitable release liner is a poly(ethylene phthalate) laminated with aluminum foil or a Tefloncoated polyester film such as sold under the designation Scotchpak 1022. The poly(ethylene phthalate) side to which the adhesive - enhancer coating is applied, is made strippable by conventional siliconizing or by other suitable means. The thickness of the adhesive - enhancer layer normally is suitable about 10 to about 200 microns, preferably about 30 to about 150 microns. The amount of enhancer in the adhesive layer depends in part on the rapidity at which it is desired that the pharmaceutical be absorbed. Generally speaking, about 1 to about 30 percent of skin permeation enhancer based on the weight of the adhesive is suitable depending upon the enhancer, adhesive polymer, desired adhesiveness and other factors. Desirably, about 5 to about 20 percent of skin permeation enhancers are used depending upon the above recited factors. The adhesive layer containing the skin permeation enhancer is transferred to the polymer matrix disc surfaces by application of lamination technique under a constant pressure. Preferably, in order to assure adequate adhesion of the adhesive polymer layer to the skin of the subject treated, an enhancer-adhesive polymer solution having a relatively low concentration of enhancer, e.g., 1-2 percent based on the weight of the adhesive polymer is used to apply a coating to the release liner. The thickness of this coating ordinarily is a minor percentage of the thickness of the final adhesive layer, such as 20-40 percent of the total adhesive polymer layer. The remainder of the adhesive polymer layer having a suitable higher concentration of the enhancer is used to coat the matrix disc layer. Suitable higher concentrations of enhancer are usually 10 to about 30 percent based on the adhesive polymer weight, the solubility and desired final amount of skin enhancer agent and other factors. The solvent of the respective coatings is removed by evaporation. The respective coatings are combined to make the final adhesive polymer-enhancer agent layer by application of constant pressure.

The four-layer transdermal pharmaceutical polymer matrix dosage units are excised. The backing layer as desired can be shaped around the sides of the dosage unit including the polymer matrix layer if such protection is desired. The resulting pharmaceutical polymer matrix dosage unit forms are then placed in appropriate packaging for storage until they are to be applied in transdermal treatment.

At least one pharmaceutical is dispersed in the polymer matrix disc layer. The type of pharmaceutical which may be dispersed in the polymer matrix disc layer includes any pharmaceutical which is capable of being transdermally or topically administered to a subject to be treated. With the controlled release of the pharmaceutical at a relatively steady rate over a prolonged period, typically 24 hours or longer, the patient is provided with the benefit of a steady infusion of the pharmaceutical over a prolonged period. As examples of pharmaceuticals which can be included in the polymer matrix disc layer of the present invention, there may be mentioned the following:

Estradiol and derivatives thereof which are biocompatible, capable of being absorbed transdermally and preferably bioconvertible to estradiol. Such derivatives of estradiol include esters, either mono- or di-esters. The monoesters can be either 3- or 17- esters. The estradiol esters can be, illustratively speaking, estradiol-3,17-diacetate; estradiol-3-acetate; estradiol-17-acetate; estradiol-3,17-divalerate; estradiol-3-valerate; estradiol-17-valerate; 3-mono, 17-mono and 3,17-dipivilate esters; 3-mono, 17-mono and 3,17-dipropionate esters; corresponding cypionate, heptanoate, benzoate and the like esters; ethinyl estradiol; estrone; and other estrogenic steroids and derivatives thereof which are transdermally absorbable.

Combinations of the above or other estradiol pharmaceuticals including the base estradiol pharmaceutical, for example, a combination of estradiol and estradiol-17-valerate or further a combination of estradiol, estradiol-17-valerate and estradiol-3,17-divalerate can be used with beneficial results. For example, 15-80% of each compound based on the total weight of the estrogenic steroid component can be used to obtain the desired result. Other combinations can also be used to obtain desired absorption and levels of estradiol in the body of the subject being treated.

It will be appreciated that the pharmaceutical may be added to the above mixture not only in the form of the pure chemical compound, but also in admixture with other pharmaceuticals which may be transdermally applied or with other ingredients which are not incompatible with the desired objective of transdermally administering the pharmaceutical to a patient. Thus, simple pharmacologically acceptable derivatives of the pharmaceuticals such as ethers, esters, amides, acetals, salts and the like, if appropriate, may be used. In some cases, such derivatives may actually be preferred. In the instance of the present invention, biologically acceptable esters have been found suitable. If an ester of estradiol or other estrogenic steroid used is employed, the selected ester is preferably more readily absorbed transdermally and is effectively bioconverted back to the basic compound after transdermal absorption, such as by naturally occurring esterase enzymes in the skin.

Frequently, it is advisable in estrogenic steroid therapy, such as estradiol therapy, to administer simultaneously an amount of a progestin. At times this simultaneous administration of a progestin is necessary in order to obtain the full benefit of the estradiol replacement therapy, e.g., premenstrual tension, dysfunctional uterine bleeding, or amenorrhea. A progestin compound found suitable for such simultaneous therapy is progesterone. Other progestin compounds from which a suitable compound can be selected are norethindrone, ethynodiol diacetate, medroxyprogesterone acetate and the like. The amount of the progestin compound administered daily and term of therapy depends upon the compound, the particular subject and the condition treated. A daily dosage for adult subjects often is in the range of about 1 mg to about 30 mg. (*Remington's Pharmaceutical Sciences*, 16th Edition, 1980, Arthur Osol et al., Eds., Mack Publishing Company pages 933-936.)

The progestin compound and the estrogenic steroid can ordinarily be compounded together in making the pharmaceutical dosage layer disc of this invention.

The skin permeation enhancers which can be used in carrying out this invention can vary. Ones that give preferred results with the polymer matrix dosage unit form having a specific pharmaceutical can vary. In some instances, the use of permeation enhancer in making a polymer matrix dosage form will result in good or even excellent absorption for one pharmaceutical, may result in no or relatively low enhancement when another pharmaceutical is used. Use of combinations of two or more of the skin permeation enhancer compounds frequently result in superior results, such as greater transdermal absorption.

Specific skin permeation enhancers which can be used in making the polymer matrix dosage forms of this invention include saturated and unsaturated fatty acids and their esters, alcohols, monoglycerides, acetate, diethanolamides and N, N-dimethylamides, such as oleic acid, propyl oleate, oleyl acetate, propyl myristate, myristyl alcohol, myristyl N, N-dimethyl amide, stearic acid and stearyl alcohol, stearyl propyl ester, monostearin, and combinations of them with, for example, 1-dodecylazacycloheptan-2-one sold under the trademark Azone by Nelson Research and Development; decyl methyl sulfoxide, dimethyl sulfoxide, salicylic acid and derivatives, N,N diethyl-m-toluamide, crotamiton, 1-substituted azacycloalkan-2-ones such as disclosed in U.S. Pat. No. 4,316,893 (the 1-substitnent having 0-17 carbon atoms, preferably, 1-11 carbon atoms), and various other compounds which are biologically compatible and have transdermal permeation activity. Ethyl alcohol and other short chain alkanols (with 1 4 carbon atoms) which have substantially the same properties and activity as ethyl alcohol do not come within the definition of skin permeation enhancer as used herein.

The above description of estradiol is primarily directed to estradiol-17-beta, which has estrogenic activity. Also, within the scope of this invention is estradiol-17-alpha, which in contrast has an estrogenic antagonist activity. The above formulating description, description regarding esters and other description also apply to estradiol-17-alpha. The dosage amount of estradiol-17-alpha or derivative thereof depends upon the need of the subject and condition being treated. The dosage administered daily often can be selected on the basis of estradiol-17-alpha from the range of from about 0.01 to about 1 mg per day.

EXAMPLES

The following examples are in illustration of the invention and are not intended to be limiting.

EXAMPLE 1

The following ingredients are used in making the pharmaceutical-containing polymer matrix discs: estradiol, 10 parts; DC 360 polysiloxane medical fluid (20 cps), 10 parts; silicone (medical-grade) 382 elastomer, 80 parts; catalyst M, 20 drops per 100g. of the mixture.

The estradiol crystals are thoroughly dispersed in the 80 parts of Silastic medical-grade 382 elastomer by using a high torque mixer (sold by Cole-Parmer Company) at about 1000 RPM.

With continued agitation, 20 parts of DC-360 (silicone medical fluid) and 20 drops (for every 100 g of the mixture) of a cross-linking agent, designated as catalyst M, which is stannous octanoate, are added to the estradiol elastomer microdispersed mixture. After each addition of the mixture, material is thoroughly mixed, and the dispersed mixture is placed under vacuum to remove entrapped air.

The estradiol-polydimethylsiloxane dispersion is placed into a device maker and is cross-linked at an elevated temperature (25°-100° C.) to form a cross-linked, medicated polymer sheet, which has a thickness of 0.2-3 mm.

The medicated polymer sheet is removed from the device maker and is cut into circular discs of about 3-20 sq. cm. The discs are attached to a backing layer of heat sealable polyester film which is laminated to aluminum foil. This laminate is sold by 3M Company as Scotchpak 1006. The medicated discs are attached using an adhesive polymer solution, which is a silicone adhesive polymer sold by Dow Corning as DC-355. Alternately, the discs can be formed directly on the backing layer and in practice are.

The silicone adhesive is believed to have the following structure:

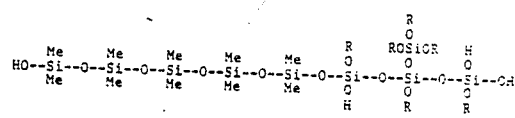

The skin permeation enhancer-adhesive film is made using the following ingredients: skin permeation enhancer, 6.5 parts; acetone 30 parts; and adhesive polymer solution, 100 parts. The skin permeation enhancer-adhesive layer is made by dissolving the 6.5 parts by weight of a skin permeation enhancer in 30 parts of acetone. The acetone solution then is added to 100 parts of a silicone adhesive solution sold by Dow-Corning under the designation DC-355.

The mixture is thoroughly mixed to form a homogeneous mixture of skin permeation enhancer and adhesive polymer, which is applied to a strip of a release liner which is a siliconized, or a Teflon-coated polyester film to permit easy removal of the release liner just prior to application of the final polymer matrix disc dosage unit to the subject to be transdermally treated. The adhesive mixture is applied at a controlled thickness. The formed layer has a thickness of about 50-200 microns. The layer is dried completely in vacuum to remove volatile matter.

The skin permeation enhancer-adhesive polymer layer with release liner is applied onto the pharmaceutical-containing polymer matrix disc with the attached backing layer under a constant pressure to provide a firmly adhered strip of a four layered structure as follows:
1. Backing layer
2. Estradiol-containing polymer matrix layer
3. Skin permeation enhancer adhesive layer
4. Release film layer which can be readily removed to permit application to the skin of the subject to receive transdermally the estradiol.

By use of an appropriate cutter, the strip is cut to provide the transdermal 17-beta-estradiol polymer matrix dosage units which are circular in shape and have an area of about 10 sq. cm.

The above polymer matrix disc dosage units are made using the following skin permeation enhancers: 1-dodecylazacycloheptan-2-one, propyl myristate and propyl oleate.

The transdermal absorption of the pharmaceutical from the pharmaceutical polymer matrix dosage units of this invention is evaluated by using a skin specimen from a "hairless" mouse or human cadaver by following the procedure described by P.R. Keshary and Y.W. Chien, in Drug Develop. & Ind. Pharm., 10 (6) 883–913 (1984).

Transdermal polymer matrix dosage units are obtained and evaluated as shown in Table I.

TABLE I

TRANSDERMAL ABSORPTION FROM POLYMER MATRIX DISC DOSAGE UNITS OF ESTROGENIC STEROID—ESTRADIOL

| Enhancers (3.2 MG/CM$^2$) | Normalized Permeation Rate (MCG/CM$^2$/HR±S.D.) | Enhancing Factors |
|---|---|---|
| None | 1.22±1.06 | 1.00 |
| Propyl Myristate | 11.38±3.38 | 9.33 |
| Propyl Oleate | 17.84±8.20 | 14.62 |
| 1-Docecylazacycloheptan-2-One | 24.61±8.93 | 20.17 |
| Decyl Methyl Sulfoxide | 15.36±0.45 | 12.59 |

EXAMPLE 2

Dosage units are made in accordance with Example 1 using the following esters of both 17-beta-estradiol and 17-alpha-estradiol: estradiol-3-acetate; estradiol-3-valerate; estradiol-17-valerate; estradiol-3-17-divalerate; estradiol-3-heptanoate; estradiol-17-propionate; estradiol-17-isopropionate; estradiol-3-propionate; estradiol-3,17-dipropionate; estradiol-3-butyrate; estradiol-17-butyrate; estradiol-3,17-dibutyrate; estradiol-17-caprate; estradiol-17-acetate; estradiol-3,17-diacetate; estradiol-17-heptanoate; estradiol-17-cypionate; estradiol-3-acetate-17-valerate. The dosage units are evaluated.

EXAMPLE 3

The following procedures and materials are used along with the processing equipment outlined as follows to make the transdermal polymer matrix dosage discs listed in this Example.

(1) In a disposable polyethylene beaker, amounts of pharmaceutical are mixed well with an aqueous solution containing a given volume fraction of polyethylene glycol (PEG) 400, using a high-torque laboratory stirrer at a high stirring rate, to form a paste.

(2) The pharmaceutical/PEG paste is added into medical-grade silicone elastomer (Silastic ® 382 elastomer, Dow Corning Corporation) and mixed well again, using a high-torque laboratory stirrer, to form a homogeneous pharmaceutical/PEG/-polymer dispersion.

(3) Adequate quantity of silicone medical fluid (DC-360, Dow Corning Corporation) is added and mixed well again.

(4) The mixture is then deaerated under vacuum at 20 psi until the entrapped air is removed.

(5) Drops of catalyst M (stannous octanoate) are added and mixed well.

(6) The mixture was again deaerated under vacuum at 20 psi until the entrapped air is eliminated.

(7) In a specially-designed device maker, the mixture is poured and spread onto a sheet of backing laminate, which is then covered with a sheet of release liner of the same size.

(8) The combination is placed between two compression plates of a thermopress, which is maintained at 60° C. and 1000 psi for 30 minutes. Spacers of different thickness are inserted between plates to control the thickness of sheeting in which the pharmaceutical component is microdispersed.

(9) The transdermal polymer matrix disc layer sheeting is removed and cut into discs of desired size and shape for further use. The following disc are made:

TABLE II

| R# | Estradiol-17-beta loading dose (% w/w of final discs) | Weight fraction of drug reservoir solution (% w/w of final discs) | Volume fraction of PEG 400 in drug reservoir solution (% v/v) |
|---|---|---|---|
| 1 | 2.5 | 5.0 | 40 |
| 2 | 5.0 | 10.0 | 40 |
| 3 | 10.0 | 20.0 | 40 |
| 4 | 5.0 | 10.0 | 30 |
| 5 | 5.0 | 10.0 | 20 |
| 6 | 5.0 | 10.0 | 10 |
| 7 | 5.0 | 10.0 | 5 |
| 8 | 5.0 | 10.0 | 0 |
| 9 | 5.0 | 2.5 | 40 |
| 10 | 5.0 | 5.0 | 40 |
| 11 | 5.0 | 7.5 | 40 |
| 12 | 5.0 | 12.5 | 40 |
| 13 | 5.0 | 15.0 | 40 |

The above disc preparations are repeated using instead of estradiol-17-beta, the following derivatives thereof and other steroids listed: estradiol-3-acetate, estradiol-17-acetate, estradiol-3,17-diacetate, estradiol-17-valerate, estradiol-17-heptanoate, estradiol-17-cypionate, estradiol-3-valerate, estradiol-3,17-divalerate, estradiol-3-acetate-17-valerate, estradiol-17-benzoate, estradiol-17-alpha (and esters corresponding to the above named esters of estradiol-17-beta).

The following dosage units of those listed in Table II are evaluated using a hydrodynamically well-calibrated skin permeation system with a freshly excised skin specimen by following the procedure described by Y.W. Chien and K.H. Valia, in Drug Develop. Ind. Pharm., 10(4) 575–599 (1984). The results are shown in Table III in which X±S.D. means the average of the permeation rates listed in column 2 with Standard Deviation:

TABLE III

| Loading Dose of Estradiol (% w/w of final disc) | Permeation Rate (mcg/cm$^2$/hr) | X±S.D. | %C.V. |
|---|---|---|---|
| 2.5 | 0.15<br>0.17<br>0.20 | 0.17±0.03 | 17.6 |
| 5.0 | 0.18<br>0.24<br>0.20 | 0.21±0.03 | 14.5 |
| 10.0 | 0.18<br>0.15<br>0.21 | 0.18±0.03 | 16.7 |

*The abdominal skin of 5- to 7-week old female hairless mouse was used.

EXAMPLE 4

The following dosage units are made following the procedures of Example 3 and are evaluated. The results are listed in Table IV:

TABLE IV

| Species | Rate of Appearance $(ug/cm^2/hr \pm SD)$ |
|---|---|
| Estradiol | $0.117 \pm 0.027$ |
| Estradiol Esters | |
| 1) Diacetate | $0.490 \pm 0.250$ |
| 2) Acetate | $0.057 \pm 0.013$ |
| 3) Valerate | $0.227 \pm 0.042$ |
| 4) Heptanoate | $0.061 \pm 0.013$ |
| 5) Cypionate | $0.016 \pm 0.002$ |

The following references disclose methods useful for making esters of hydroxy-substituted steriods such as estradiol and other estrogenic steriods. *Chem. Pharm. Bull.*, 29(11), 3202–7 (1981); *Tetrahedron Lett.*, (26), 2431–2 (1979); *J. Org. Chem.*, 44(4), 654–6 (1979); *Invest. Urol.*, 17(6), 506–9 (1980); U.S. Pat. No. 3,478,070, issued Nov. 11, 1969 to Stein, Reinhardt Peter, et al.; *Yao Hsueh Hsueh Pao*, (14(6), 343–8 (1978); *Aust. J. Biol. Sci.*, 24(6), 1263–75; U.S. Pat. No. 3,496,272, issued Feb. 17, 1980 to Kruger, Gunther; *Farmaco, Ed. Sci.*, 28(3), 186–202 (1973); *Am. J. Anim. Sci.*, 48(3), 449–53 (1968).

EXAMPLE 5

The procedure of Example 3 is repeated to produce transdermal polymer matrix dosage units in which an effective amount of a progestin is incorporated into the microdispersion along with an effective amount of ethinyl estradiol, estradiol-17-beta or one or more ester derivatives named above either with or without base compound estradiol-17 -beta. The following combinations are illustrative of pharmaceutical combinations made:

(a) Ethynodiol diacetate/ethinyl estradiol, 1 mg/50 mcg,
(b) Ethynodiol diacetate/mestranol, 1 mg/100 mcg,
(c) Norethindrone/mestranol, 1/20, 1/50, 1/80, 1.5/30, 2/100, and 10/60 (mg/mcg),
(d) Norethindrone acetate/ethinyl estradiol, 2.5/50, 1.5/30, 1/50 and 1/20 (mg/mcg),
(e) Norethynodrel/mestranol, 2.5/100, 5/75, and 9.85/150 (mg/mcg),
(f) Norgestrel/mestranol, 500/50 and 300/30 (mcg/mcg).

Hydroxyprogesterone caproate or other suitable ester, medroxyprogesterone acetate or other suitable ester, dydrogesterone, or progesterone can also be used as the progestin in an appropriate amount.

EXAMPLE 6

The above example 3 is repeated except that an adhesive polyurethane foam disc is applied to the exposed surface of the backing layer, the backing layer is shaped around the edge of the pharmaceutical polymer matrix disc layer to protect the side thereof. An adhesive layer may be applied to the surface of the pharmaceutical containing disc. The adhesive used is a silicone adhesive, polyacrylic adhesive or a polyisobutylene adhesive, which is biocompatible and permits the pharmaceutical component of the pharmaceutical polymer matrix disc to be transdermally absorbed. If desired, one or more skin permeation enhancer agents are incorporated into the adhesive layer in an effective amount. Alternatively or additionally, one or more skin permeation enhancer agents can be incorporated into the pharmaceutical polymer matrix disc layers.

EXAMPLE 7

The procedures of Examples 3 and 6 are repeated using respectively polyisobutylene, polydimethylsiloxane-polyvinylmethylsiloxane block and graft copolymers, polydimethylsiloxane-polymethylvinylsiloxane copolymers, polymethylsiloxane-polyethylenesilane block and graft copolymers, polydimethylsiloxane-polymethacrylate block and graft copolymers, polydimethylsiloxane-polyethylene oxide block and graft copolymers, polymethylpropylsiloxane, polydimethylsiloxane-polyvinylacetate block and graft copolymers, polydimethylsiloxane-polyethylene copolymers, polydimethylsiloxane-polycarbonate block and graft copolymers in forming the transdermal pharmaceutical polymer matrix discs.

What is claimed is:

1. A transdermal pharmaceutical-containing polymer matrix dosage unit having the following components:
   (a) a backing layer which is substantially impervious to the pharmaceutical to be delivered transdermally;
   (b) a polymeric matrix disc layer which is adhered to said backing layer and which has microdispersed therein an amount of a pharmaceutical selected from the group consisting of an estradiol; non-estradiol estrogenic steriods capable of transdermal absorption and which will provide a dosage amount of said pharmaceutical to be delivered transdermally; esters thereof which are absorbable by the skin of the subject being treated and which are bioconvertible after transdermal absorption to estradiol or said non-estradiol estrogenic steriods; and pharmaceutically effective combinations thereof; and
   (c) an adhesive means for securing the dosage unit to the subject treated for transdermal absorption and which has distributed therein an amount in the range from zero up to an effective amount of one or more skin permeation enhancers to provide substantial skin absorption enhancement for said pharmaceutical;
   said polymeric matrix disc layer covered by and adhered to said adhesive means or being in direct contact with the skin of the subject treated.

2. A transdermal pharmaceutical polymer dosage unit of claim 1 wherein the polymer matrix disc layer is made from a silicone polymer or copolymer.

3. A transdermal pharmaceutical polymer dosage unit of claim 2 wherein the silicone polymer or copolymer is a methyl silicone polymer or copolymer.

4. A transdermal pharmaceutical polymer matrix dosage unit of claim 1 wherein the polymer matrix disc layer is a cross-linked polysiloxane polymer of the following formula:
wherein R is selected from the group consisting of alkyl or alkoxy having 1–7 carbons atoms, vinyl or phenyl; and wherein n is about 100 to about 5,000.

5. A transdermal pharmaceutical polymer matrix dosage unit of claim 2 wherein the matrix is made up of microdispersed compartments having a crossectional dimension of from about 10 to about 200 microns.

6. A transdermal dosage unit of claim 1 wherein the pharmaceutical is selected from the group consisting of estradiol-17-beta; estradiol-17-alpha; mono- or di-esters thereof which are capable of transdermal absorption and which upon absorption by the skin are bioconverted by the skin to remove the ester groups; or pharmaceutically effective combinations thereof.

7. A transdermal dosage unit of claim 2 wherein the pharmaceutical is selected from the group consisting of estradiol-17-beta; estradiol-17-alpha; mono- or di-esters thereof which are capable of transdermal absorption and which upon absorption by the skin are bioconverted by the skin to remove the ester groups; or pharmaceutically effective combinations thereof.

8. A transdermal dosage unit of claim 3 wherein the pharmaceutical is selected from the group consisting of estradiol-17-beta; estradiol-17-alpha; mono- or di-esters thereof which are capable of transdermal absorption and which upon absorption by the skin are bioconverted by the skin to remove the ester groups; or pharmaceutically effective combinations thereof.

9. A transdermal dosage unit of claim 4 wherein the pharmaceutical is selected from the group consisting of estradiol-17-beta; estradiol-17-alpha; mono- or di-esters thereof which are capable of transdermal absorption and which upon absorption by the skin are bioconverted by the skin to remove the ester groups; or pharmaceutically effective combinations thereof.

10. A transdermal dosage unit of claim 6 wherein the matrix has microdispersion pharmaceutical compartments having a cross-sectional dimension of from about 10 to about 200 microns.

11. A transdermal dosage unit of claim 10 wherein a polyethylene glycol dispersing agent is present in the microdispersed pharmaceutical compartments.

12. A transdermal dosage unit of claim 6 wherein the pharmaceutical is estradiol-17-beta.

13. A transdermal dosage unit of claim 7 wherein the pharmaceutical is selected from the group consisting of combinations of estradiol-17-beta and one or more of said esters of estradiol-17-beta.

14. A transdermal dosage unit of claim 7 wherein the pharmaceutical is selected from the group consisting of combinations of two or more esters of estradiol-17beta.

15. A transdermal dosage unit of claim 7 wherein the pharmaceutical is selected from the group consisting of combinations of two or more esters of estradiol-17-beta or combinations of estradiol-17-beta and one or more of said esters of estradiol-17-beta, at least one of said esters of said combinations being estradiol valerate.

16. A transdermal dosage unit of claim 6 wherein the pharmaceutical is estradiol-17-alpha.

17. A transdermal estrogenic pharmaceutical-containing polymer matrix dosage having the following components:
(a) a backing layer which is substantially impervious to the pharmaceutical to be delivered transdermally;
(b) a polymeric matrix disc layer which is adhered to said backing layer and which has microdispersed therein an amount of a pharmaceutical selected from the group consisting of estradiol-17-beta; non-estradiol estrogenic steriods capable of transdermal absorption and which will provide a dosage amount of said pharmaceutical to be delivered transdermally; esters thereof which are absorbable by the skin of the subject being treated and which are bioconvertible after transdermal absorption to estradiol or said non-estrogenic estrogenic steriods; and combinations thereof; said microdispersed pharmaceutical also comprising a pharmaceutically effective amount of a progestin; and
(c) an adhesive means for securing the dosage unit to the subject treated for transdermal absorption and which has distributed therein an amount in the range from zero to an effective amount of one or more skin permeation enhancers to provide substantial skin absorption enhancement for said pharmaceutical;
said polymeric matrix disc layer covered by and adhered to said adhesive means or being in direct contact with the skin of the subject treated.

18. A transdermal, estrogenic pharmaceutical-containing polymer matrix dosage unit of claim 17 wherein the pharmaceutical is selected from the group consisting of estradiol-17-beta; esters of estradiol-17-beta; combinations of two or more esters of estradiol-17-beta; and combinations of estradiol-17-beta and one or more esters thereof.

19. A process of estradiol-17-beta replacement therapy by applying to the skin of a subject needing said therapy a dosage unit as described in claim 1.

20. A process of claim 19 wherein the pharmaceutical is selected from the group consisting of estradiol-17-beta; esters of estradiol-17-beta; combinations of two or more estersof estradiol-17-beta; and combinations of estradiol-17-beta and one or more esters of estradiol-17-beta.

* * * * *

UNITED STATES PATENT AND TRADEMARK OFFICE
CERTIFICATE OF CORRECTION

PATENT NO. : 4,883,669
DATED : November 28, 1989
INVENTOR(S) : Yie W. Chien, et al.

It is certified that error appears in the above-indentified patent and that said Letters Patent is hereby corrected as shown below:

In Column 16, line 60 of Claim 4, the following should be included after-- formula --

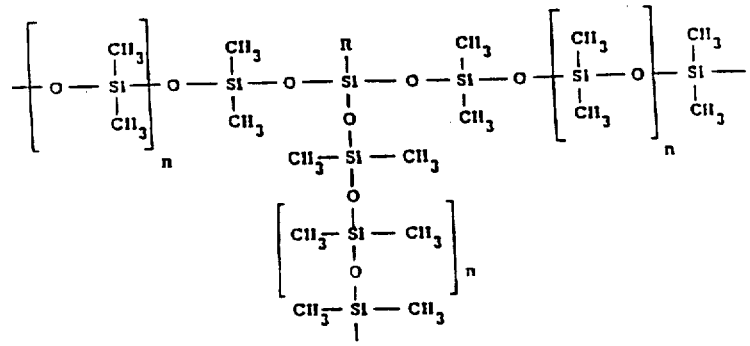

In Column 15, line 9, the following should be changed:

"ug should be changed to mcg"
The text should read as follows: (mcg/cm$^2$/hr$\pm$SD)

Signed and Sealed this

Seventh Day of November, 1995

Attest:

BRUCE LEHMAN

Attesting Officer

Commissioner of Patents and Trademarks